United States Patent [19]

Calcote et al.

[11] 4,278,441
[45] Jul. 14, 1981

[54] FLAME SAMPLING APPARATUS AND METHOD

[75] Inventors: Hartwell F. Calcote, Princeton; Douglas B. Olson, Lawrenceville, both of N.J.

[73] Assignee: Aerochem Research Laboratories, Inc., Princeton, N.J.

[21] Appl. No.: 121,295

[22] Filed: Feb. 14, 1980

[51] Int. Cl.³ .......................................... G01N 21/72
[52] U.S. Cl. .................... 23/232 E; 422/54; 422/80
[58] Field of Search ............ 23/232 R, 232 E, 230 R, 23/230 PC; 422/54, 78, 80; 73/421.5, 23, 26

[56] References Cited

U.S. PATENT DOCUMENTS

| | | | |
|---|---|---|---|
| 3,141,741 | 7/1964 | Hoel et al. | |
| 3,208,333 | 9/1965 | Gilbert, Jr. | |
| 3,425,806 | 2/1969 | Karmen | 422/54 X |
| 3,451,780 | 6/1969 | Prescott et al. | 23/232 E X |
| 3,597,162 | 8/1971 | Reinecke | 23/232 E X |
| 3,740,154 | 6/1973 | Green | 356/187 |
| 3,879,126 | 4/1975 | Delew | 356/87 |
| 3,917,405 | 11/1975 | Hartmann et al. | 356/87 |
| 3,955,914 | 5/1976 | Delew | 356/187 X |
| 4,097,239 | 6/1978 | Patterson | 23/232 R |
| 4,148,931 | 4/1979 | Reuschel et al. | 23/232 E |

*Primary Examiner*—Ronald Serwin
*Attorney, Agent, or Firm*—Richard C. Woodbridge

[57] ABSTRACT

A mass spectrometer is employed to analyze the boron and phosphorus content in silicon or a silicon compound such as $SiH_4$ or $SiHCl_3$. According to the preferred embodiment a first non-seeded flame is surrounded by a second seeded flame. The velocities of both flames are approximately the same so that the boundary between them is relatively stable. Small quantities of $BO_2^-$ and $PO_2^-$ are formed in the second flame seeded with a silicon compound. The positively charged inlet orifice of a mass spectrometer is placed in the first flame sufficiently close to the boundary so as to attract negative ions into the instrument. In this manner the relatively small orifice of the sampling cone is not plugged by the $SiO_2$ particles that are generated in the outer flame and the boron and phosphorus content of the silicon or silicon compound can be measured.

10 Claims, 6 Drawing Figures

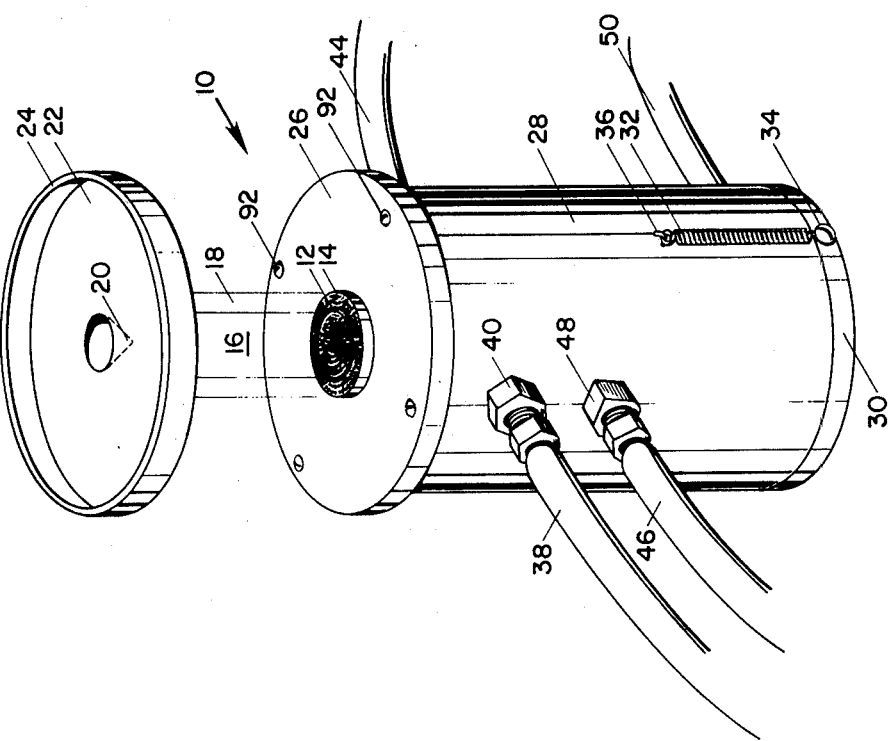

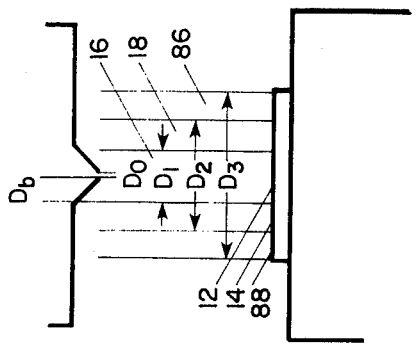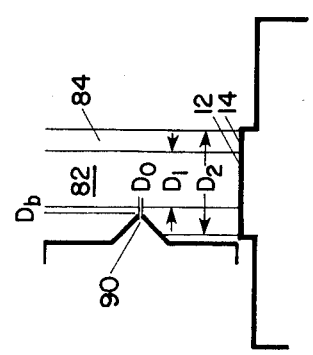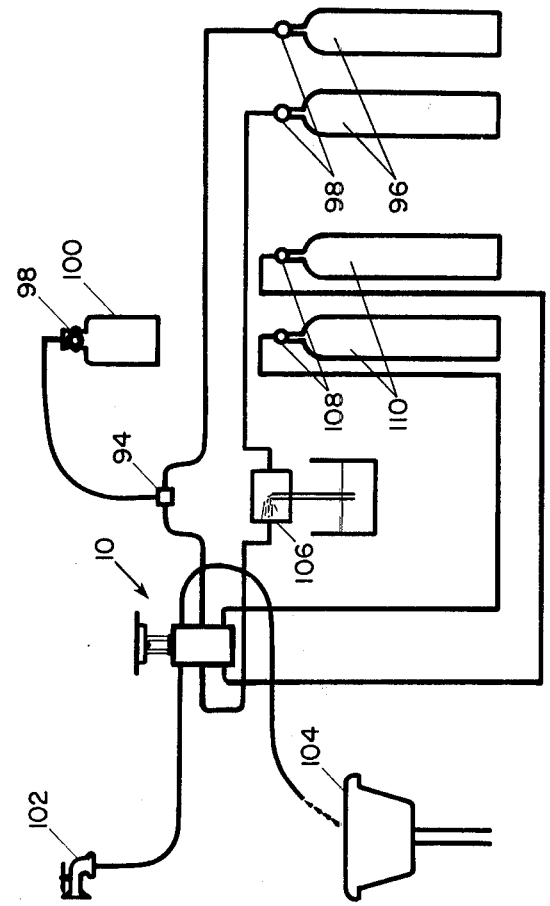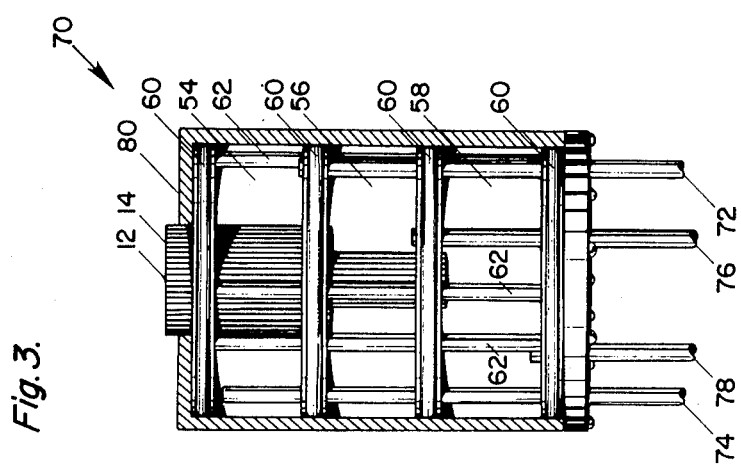

FLAME SAMPLING APPARATUS AND METHOD

BACKGROUND OF THE INVENTION

1. Field of the Invention

This invention relates to a dual flame method and apparatus for performing flame ion mass spectrometry.

2. Description of the Prior Art

In general the clogging of the orifice of a mass spectrometer sampling cone by $SiO_2$ particles is a relatively novel problem about which little is written. However, concentric gas flows are, of course, well known in other arts and in the technical literature. There also are techniques known in the prior art for analyzing materials in concentric gas flows.

For example, U.S. Pat. No. 3,208,333 issued to Gilbert discloses a method for operating an atomizer burner for spectro-chemical measurement. The burner provides free concentric gas flows about a sample conduit. The inner gas flow provides the aspirating and atomizing action and the outer gas flow functions as a sheet separating the flame and surrounding atmosphere.

U.S. Pat. No. 3,141,741 issued to Hoele et al and U.S. Pat. No. 3,740,154 issued to Green disclose burners for use in analytical procedures where coaxially disposed tubes and ducts separately supply a burner kit with sample and flame gases respectively.

U.S. Pat. No. 3,879,126 issued to DeLew and U.S. Pat. Nos. 3,955,914 and 3,917,405 issued to Hartmann et al teach a flame photometric detection technique in which the sample to be analyzed is delivered to the tip of the burner separately from the combustion gases so that the sample is burned at the peripheral region of the flame.

U.S. Pat. No. 4,097,239 issued to Patterson discloses a two-flame burner for use in flame photometric detection in which a sample is burned in a first flame and the combustion products are subsequently combusted in a spacially separated second flame.

SUMMARY OF THE INVENTION

Briefly described the invention comprises a method and apparatus for determining the boron and phosphorus content of silicon or a silicon compound, such as $SiH_4$ or $SiHCl_3$. The analysis is based on the formation of negative ions $BO_2^-$ and $PO_2^-$ which are analyzed by a mass spectrometer. As a by-product relatively large quantities of small $SiO_2$ (sand) particles are generated. If sampled in the conventional manner the orifice of the sampling cone of the mass spectrometer repeatedly becomes clogged by the particles of $SiO_2$. The size of the orifice in a typical sampling cone is in the range of 2-10 mils.

The basic concept of the invention is to avoid the problem of clogging the sampling cone orifice with $SiO_2$ by placing the sampling cone of the mass spectrometer in a flame which does not contain the silicon sample to be analyzed adjacent to the flame containing the sample. It is important that the demarkation line or boundary between the seeded (i.e., containing the silicon or silicon compound to be analyzed) and unseeded flames be relatively sharp and stable so that the mass spectrometer sampling cone can be brought close to the seeded flame. A relatively sharp boundary can be obtained by making the velocities of the seeded and non-seeded flames nearly the same. A small positive potential on the mass spectrometer sampling cone will draw the negative ions to the cone, leaving the $SiO_2$ particles behind in the outer flame. According to the preferred embodiment an outer seeded flame concentrically surrounds an inner non-seeded flame in which the sampling cone is located. While the invention has particular utility in the analysis of B and P in silicon or silicon compounds, it also has general applicability to the problem of sampling either positive or negative ions from a flow containing particles that could clog a sampling orifice.

The invention can be further understood with reference to the following drawings and detailed description of the preferred embodiment.

BRIEF DESCRIPTION OF THE DRAWINGS

FIG. 1 is a perspective view of the preferred embodiment of the invention.

FIG. 2 is a cross-sectional view of the preferred embodiment illustrated in FIG. 1.

FIG. 3 is a cross-sectional view of an alternative embodiment of the invention for use at pressures less than atmospheric.

FIG. 4 is a schematic illustration showing an alternative method of sampling the seeded flame with an orifice that is parallel to the flow of the combustion gases.

FIG. 5 is another alternative embodiment of the invention in which a third non-seeded flame surrounds a second seeded flame which in turn surrounds an inner non-seeded flame.

FIG. 6 is a highly abstract illustration of the entire system incorporating the preferred embodiment of the burner illustrated in FIG. 1.

DETAILED DESCRIPTION OF THE INVENTION

During the course of this description like numbers will be used to indicate the same elements according to the six drawings which illustrate the apparatus and method.

The specific invention covered by this application can be best understood by relating it to the analytical problem in which the need, covered by the invention, arose.

All self-sustaining combustion flames of $H_2$, hydrocarbons, or CO convert boron additives to $HBO_2$ accompanied by much smaller quantities of $BO_2$; phosphorus compounds react and oxidize to produce a mixture of PO and $PO_2$ with traces of P and $HPO_2$. If these flames are seeded with a source of electrons, such as an easily ionizable alkali metal salt, a number of electron attachment reactions take place to produce the relatively stable negative ions $BO_2^-$ and $PO_2^-$. The kinetics of negative ion production are reasonably rapid at flame temperatures $> \simeq 2000$ K. and local equilibrium with respect to charged spcies is closely approached, i.e., the reactions

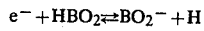

$$e^- + HBO_2 \rightleftharpoons BO_2^- + H$$

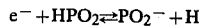

$$e^- + HPO_2 \rightleftharpoons PO_2^- + H$$

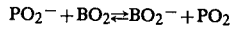

$$PO_2^- + BO_2 \rightleftharpoons BO_2^- + PO_2$$

are balanced despite the fact that there are small, known deviations from equilibrium on the part of electron and H-atom concentrations.

Thus when silicon or a silicon compound containing boron or phosphorus impurity is added to a flame containing electrons, the boron or phosphorus forms negative ions as above which can be detected by ion mass spectrometry down to extremely small concentrations.

For reasons which are not germane to this discussion, hydrogen and carbon monoxide are the most useful fuels for supporting such flames. Neither of these flames contain free electrons so that the electrons are produced by seeding the flame with an easily ionizable substance such as an alkali metal. Both potassium and cesium have been used for this purpose. Electrons are then produced by the equilibrium process. e.g., $$Cs \rightleftarrows Cs^+ + e^-$$

which is strongly dependent upon the temperature. The cesium has been added as a solution of cesium nitrate in water and a water aspirator used to atomize the salt solution into the burner flame gases.

The ultimate sensitivity of the system is, of course, directly dependent upon the quantity of silicon sample added to the flame. Silicon also reacts in the flame:

$$Si + O_2 \rightarrow SiO_2$$

Unfortunately, $SiO_2$ is a solid (sand) and clogs the mass spectrometer sampling cone. As one increases the sample added to the flame the operating time before the sampling cone clogs becomes annoyingly short, i.e., measured in minutes for practical quantities of sample addition, of the order of 1% of the total fuel-air mixture. This would, of course, make the above analytical technique useless for practical purposes. The invention described herein solves the problem by devising a method and apparatus by which the desired ions, $BO_2^-$ and $PO_2^-$ are deflected by an electric field into the mass spectrometer sampling cone without having the $SiO_2$ particles impinge upon the cone.

As shown in FIGS. 1 and 2 the invention 10, according to the preferred embodiment thereof, includes an inner nozzle 12 and an outer nozzle 14 which respectively generate an inner non-seeded flame 16 and an outer seeded flame 18. Flame 18 is seeded with both the sample and an alkali salt as described above. The sampling cone 20 is located directly in the path of flame 16 and oriented in a perpendicular relationship thereto. Cone 20 includes a small sampling orifice 90 having a typical diameter in the range of 2-10 mils. In this embodiment of the invention, it is necessary that the sampling cone 20 and cover 22 do not form an electrical short circuit between the sampling orifice 90 and the outer seeded flame 18. Such an electrical short would prevent the application of an electrical field between cone 90 and flame 18. Thus, the tip of the cone 90 is made an electrical conductor and the body of the cone 20 an electrical insulator by coating the tip of a quartz cone with a small ring of platinum which is connected to a d.c. power supply through a wire inside the cone in a spiral following the cone shape (not shown). The spiral arrangement avoids an electric field inside the cone which would deflect the ions to one side. There are also other ways that would be acceptable for insulating the cone 20 from the cover 22. The structure described above is believed to be known and is presented for the purpose of illustration only. A cover 22 including a rim 24 serves as a base for sampling cone 20. The foregoing apparatus is in turn connected to a conventional mass spectrometer which is abstractly illustrated in FIG. 2 as element 52. In the test laboratory a quadrapole instrument was used.

The body of the burner invention 10 includes a top lid section 26, a cylindrical body section 28 and a lower flat bottom section 30. Lid 26 is connected to body 28 by a plurality of small machine screws 92. An O-ring 60 similar to the ones illustrated in FIG. 2 is employed to form a seal between top lid 26 and cylindrical body 28. Similarly, the bottom 30 is sealed with respect to cylindrical body 28 by another O-ring 60. However, bottom 30 is spring-loaded by spring 32 so that if there is an internal explosion the bottom 30 will harmlessly blow off. Spring 32 is connected between a hook 36 attached to body 28 and a machine screw 34 connected directly to bottom 30. Burner 10 is divided into three internal chambers 54, 56 and 58 respectively as shown in detail in FIG. 2. The top chamber 54 comprises a small upper water jacket to dissipate the heat generated at burner nozzles 12 and 14. Cool water enters upper chamber 54 through water inlet line 38 and a standard fitting 40. The water exits through orifice 42 and water output line 44. As shown in FIG. 6, an abstract faucet 102 is shown supplying water to burner 10. The burner heated water then exits to an abstractly illustrated sink 104. Water cooling is necessary to prevent the device from overheating.

Intermediate chamber 56 feeds the outer flame 18. A gas input line 46 enters the second chamber 56 through a standard fitting 48 similar to fitting 40 previously described. A mixture of combustile gases and the sample of material to be tested is fed in through gas line 46 into chamber 56. A fine mist of alkali metal salt solution (typically 0.2 mol $1^{-1}$ $CsNO_3$ in water) is also fed through gas line 46 to the chamber 56. Chamber 56 is sealed from upper water chamber 54 by a disc-shaped barrier and another sealing O-ring 60. The pressure of the gas and sample mixture in chamber 56 causes the combination to rise through a plurality of small tubes 64 which emerge through annular nozzle 14. Tubes 64 comprise approximately 44 small stainless steel hypodermic tubes. The purpose of the arrangement is to maintain a steady flame.

Flame 18 is generated above nozzle 14 and eventually impinges against surface 22. Outer flame 18 typically includes ions of $BO_2^-$ or $PO_2^-$ along with $SiO_2$ particles. The $SiO_2$ particles do not clog orifice 90 because they do not impinge directly upon sampling cone 20. According to the preferred embodiment the sampling cone 20 is positively charged and the body of the burner invention 10 is grounded.

The third chamber 58 feeds an inner set of approximately 19 hypodermic tubes 66 which form nozzle 12 at the upper ends thereof. Chamber 58 is fed with a non-seeded combustible gas combination through gas line 50 and an orifice 68. The flow of seeded gas through lines 46 and non-seeded gas through lines 50 is adjusted so that the linear velocities $V_1$ and $V_2$ of the flames 16 and 18 respectively are substantially the same. That condition makes the boundary between flames 16 and 18 relatively stable and predictable in location. Lastly, a plurality of support rods 62 are employed to strengthen the structure and maintain the distance between the chamber separators.

In the preferred embodiment of the invention the inner flame 16 has a cross-sectional diameter of approximately 0.5 centimeters. It may range from approximately 0.25 to 0.5 centimeters. The outer flame 18 similarly has an outside diameter of approximately 1 centimeter. Accordingly, the distance from the sampling orifice hole 90 to the boundary between the flames 16 and 18 is in the neighborhood of 0.1 to 0.3 centimeters. Approximately 19 stainless steel hypodermic tubes 66 were used to feed nozzle 12 of which they are a part. Approximately 44 stainless steel hypodermic tubes 64 were employed to feed the outer nozzle 14. While the orifice 90 of the mass spectrometer may range from 2 to 10 mils the one employed according to the preferred embodiment was approximately 3 mils. The voltage on sampling cone 20 is preferably in the range of 50 to 300 volts positive. The distance from the surface of burner nozzle 12 and 14 to the sampling cone orifice 90 is between 2 and 4 centimeters. The outside diameter range for the outer nozzle is between 1 and 3 centimeters.

A combination of hydrogen/oxygen/nitrogen mixed in a ratio of 3.5/½ is the preferred combustible gas combination. The inner gas flow was about 100 cm$^3$ s$^{-1}$ and the outer gas flow about 310 cm$^3$ s$^{-1}$.

It is relatively easy to meter the sample material if the material is a gas. For example, if silane is used it is only necessary to measure the gas flow with conventional instruments.

If a liquid is to be tested it is typically injected with a syringe into a hot chamber where it evaporates so that it can be readily transported in the gas flow to burner nozzle 14.

If the material to be tested is a hard solid sample, then the task is considerably more difficult. One novel solution to this problem was developed by Jonathan Allen along with Robert K. Gould. That invention comprises a grinding apparatus which can be adjusted to pulverize the sample specimen at a predictable rate and inject the small particles so produced either directly into a sampling flame or into the gas lines that feed the flame. The device just described is the subject of a co-pending patent application entitled "Method and Apparatus for Pulverizing Solid Materials with a Grindstone and Injecting Particles Thereof into a Flame for Analysis". The techniques of mixing combustion gases and feeding sample gases or sample liquids into a gas feed line of a burner are not new. However, the injection of pulverized particles into a flame either directly or into the gas line that feeds the flame by means of a grinding device is believed to be entirely novel.

An alternative embodiment 70 of the present invention is illustrated in cross-sectional view in FIG. 3. The burner 70 is designed for lower pressure applications and differs from the burner 10 in several respects. Firstly, nozzles 12 and 14 are broader therefore providing a larger burner surface. This is necessary because the flame becomes thicker at lower pressures. That is to say that the blue zone becomes greater. Conversely the higher the pressure the thinner the blue zone. Lower pressure burner 70 is fed through its bottom end by tubes 72, 74, 76 and 78. This is in contrast to the burner 10 illustrated in FIG. 1 which is entirely side fed. Water cooling chamber 54 is fed by water inlet pipe 72. Water exits from chamber 54 through water outlet pipe 74. The seeded gas is fed by inlet pipe 76 to chamber 56 where it proceeds through the hypodermic tubes to nozzle surface 14. The inner flame 12 is fed through inlet pipe 78 which communicates with the lower chamber 58. Note also that the body 80 of the low pressure burner 70 includes an upper surface which is integral with the side surface. In contrast, the burner 10 of FIG. 1 includes a separate upper lid 26 which is attached by machine screws 92 to a cylindrical body 28. As in the device of FIG. 1, chambers 54, 56 and 58 are separated by disc-like dividers having O-rings 60 on the circumference thereof. A plurality of rods 62 serves to space the chamber separators apart and provide additional rigidity for the structure.

Another alternative method of sampling is illustrated in FIG. 4. According to that embodiment the inner flame 82 is seeded and the outer annular flame 84 is non-seeded. A sampling orifice 90 having a diameter $D_o$ is placed in the non-seeded outer flame 84 a distance $D_b$ from the boundary between the seeded inner flame 82 and the non-seeded outer flame 84. The distance $D_b$ would preferably be in the neighborhood of 0.1 centimeters.

FIG. 5 is an abstract schematic of an improved version of the preferred embodiment illustrated in FIG. 1. The only difference is in the addition of a third non-seeded outer flame 86 which is produced by a third annular burner nozzle 88. The preferable width of the third non-seeded outer flame 86 is about ¼ of a centimeter. Therefore the total maximum outside burner diameter might be in the neighborhood of 1.5 centimeters. The advantage of the third outer flame 86 is that it protects the sample materials in the seeded second flame 18 from being contaminated by impurities in the surrounding atmosphere.

In its broadest sense the invention can be practiced in two flat parallel flames. That would, of course, be the limiting case of an infinitely large burner such as that disclosed in the preferred embodiment.

FIG. 6 is a very abstract schematic illustrating the inter-connection of the major elements of the system when associated with the burner 10 of the preferred embodiment. As previously described water from a conventional cold water source 102 feeds the upper water jacket chamber 54 and exits into a suitable receptacle such as a sink 104. The combustible gas and oxidizer gas for chamber 56 come from industrial bottles 96 and are controlled by conventional flow regulators 98. The oxidizer line proceeds from the source through an atomizer 106 to burner 10. The fuel line is shown going to a special mixing station 94 which is connected to a sample source 100 through regulator device 98. The source 100 could be a gas bottle containing silane to be analyzed which directly mixes with the fuel at station 94 before it enters chamber 56 of burner 10. As previously described a liquid could be injected through the use of an appropriate vaporizer. Similarly, hard solid particles can be injected through the use of a device such as that described in the previously mentioned patent application by Jonathan Allen and Robert K. Gould.

The fuel and oxidizer for chamber 58 come from industrial bottles 110 through conventional regulators 108.

The flame cones generated are similar to those found on a conventional Meeker burner. It has been found that small hypodermic tubing 64 and 66 produces the smoothest flow. Alternatively an acceptable burner nozzle can be fashioned by spirally wrapping corrugated metal so as to form a plurality of small regular channels to replace hypodermic tubes 64 and 66. While a hydrogen/oxygen/nitrogen combination has been described as the preferred combustible gas there are other combinations that will work too. For example, carbon monoxide and air could also be employed. It is further possible that the combustible gases employed in the inner and outer flames can be different just as long as the difference does not change the character of the experiment.

The invention just described finds special applicability in testing to determine the amount of boron or phosphorus in a silicon or silicon compound. It will be appreciated by those of ordinary skill in the art that other analyses where solid particle by-products present a problem could utilize this invention as well. This particular instrument has the advantage that it can detect very small quantities of boron or phosphorus in silicon without having the nozzle 90 clogged with the $SiO_2$ by-product.

While the invention has been described with reference to a preferred embodiment thereof it will be appreciated by those of ordinary skill in the art that changes can be made to the structure and function of the device without departing from the spirit and scope thereof.

We claim:

1. A flame sampling apparatus comprising:
   a first flame means for producing a first flame including a sample to be analyzed, said first flame having a velocity $V_1$;
   a second flame means for producing a second flame having a velocity $V_2$ close in magnitude to $V_1$, said first and second flames having a relatively stable boundary therebetween; and,
   an analyzing means including a charged orifice located in said second flame and positioned close enough to said boundary to attract sample ions of the opposite polarity to the charge on said orifice from said first flame into said orifice for analysis by said analyzing means.

2. The apparatus of claim 1 wherein said second flame is concentrically surrounded by said first flame.

3. The apparatus of claim 2 wherein said first flame means and said second flame means include a nozzle which includes a plurality of small diameter tubes which impart a relatively smooth characteristic to the flow of gases which feed said first and second flames.

4. The apparatus of claim 1 wherein said ions of said sample comprise $BO_2^-$.

5. The apparatus of claim 1 wherein said ions of said sample comprise $PO_2^-$.

6. The apparatus of claim 1 further comprising:
   a third flame means concentrically surrounding said first and second flame means.

7. The apparatus of claim 1 wherein said first flame is concentrically surrounded by said second flame.

8. A method for sampling ions in a flame comprising the steps of:
   producing a first flame containing the ion samples to be analyzed, said first flame having a velocity $V_1$;
   producing a second flame located adjacent to said first flame and having a velocity $V_2$ close in magnitude to $V_1$, said first and second flames defining a relatively stable boundary therebetween; and,
   sampling said ions of said sample with an analyzing means having a charged orifice located in said second flame and positioned at a distance close enough to said boundary to attract ion samples of a polarity opposite to the charge on said orifice thereby drawing the sample ions into said orifice for analysis by said analyzing means.

9. The method of claim 8 further comprising the step of:
   surrounding said second flame by said first flame.

10. The method of claim 8 further comprising the step of:
    surrounding said first flame with a third flame.

* * * * *